US006346536B1

(12) United States Patent
Li et al.

(10) Patent No.: US 6,346,536 B1
(45) Date of Patent: *Feb. 12, 2002

(54) POLY(ADP-RIBOSE) POLYMERASE INHIBITORS AND METHOD FOR TREATING NEURAL OR CARDIOVASCULAR TISSUE DAMAGE USING THE SAME

(75) Inventors: Jia-He Li, Cockeysville; Paul F. Jackson, Bel Air; Keith M. Maclin, Baltimore; Jie Zhang, Ellicott City, all of MD (US)

(73) Assignee: Guilford Pharmaceuticals Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/922,548

(22) Filed: Sep. 3, 1997

(51) Int. Cl.$^7$ .................. A61K 31/44; C07D 515/00; C07D 311/88; A01N 25/28

(52) U.S. Cl. .................. 514/286; 514/288; 546/66; 546/72; 546/76; 549/224; 549/384; 424/418; 424/419; 424/420

(58) Field of Search .................. 514/286, 288; 546/66, 72, 76; 549/224; 424/418–420

(56) References Cited

U.S. PATENT DOCUMENTS

| 932,290 A | 8/1909 | Kacer et al. | |
| 1,001,325 A | 8/1911 | Ullman et al. | 260/250 |
| 1,253,252 A | 1/1918 | Kardos et al. | 260/250 |
| 1,880,441 A | 10/1932 | Heidenreich et al. | 260/250 |
| 1,895,105 A | 1/1933 | Rath et al. | 260/288 |
| 2,467,692 A | 4/1949 | Petrow | 260/288 |
| 2,593,798 A | 4/1952 | Robinson | 260/286 |
| 2,612,503 A | 9/1952 | Ullyot | 260/288 |
| 2,638,472 A | 5/1953 | Grewe | 260/286 |
| 2,666,059 A | 1/1954 | Davis et al. | 260/288 |
| 2,700,040 A | 1/1955 | Ullyot | 260/286 |
| 2,892,841 A | 6/1959 | Rudner | 260/288 |
| 2,992,220 A | 7/1961 | Irving et al. | 260/250 |
| 3,247,212 A | 4/1966 | Johnson | 260/287 |
| 3,291,801 A | 12/1966 | Montgomery | 260/289 |
| 3,300,499 A | 1/1967 | Lesher | 260/287 |
| 3,403,157 A | 9/1968 | Humber et al. | 260/288 |
| 3,507,872 A | 4/1970 | Hegar | 260/286 |
| 3,534,038 A | 10/1970 | Machatzke et al. | 260/256.4 |
| 3,557,119 A | 1/1971 | Humber | 260/287 |
| 3,573,304 A | 3/1971 | Eberle et al. | 260/250 |

(List continued on next page.)

FOREIGN PATENT DOCUMENTS

| BE | 562948 | 6/1960 |
| BE | 628255 | 2/1963 |
| CA | 1000701 | 11/1976 |
| CA | 1274339 | 7/1987 |
| CA | 1278141 | 10/1987 |
| CH | 463-778 | 10/1965 |
| CH | 463 778 | 10/1965 |
| DE | 282711 | 3/1915 |
| DE | 963 184 | 5/1957 |
| DE | A-211910 | 3/1971 |
| DE | 2111910 | 3/1971 |
| DE | A-2429515 | 6/1973 |
| DE | 24-29515 | 1/1975 |
| DE | 26 50 226 | 5/1978 |
| DE | 33 32 633 A | 4/1985 |
| EP | 0 005 232 A | 11/1979 |
| EP | 0 126 684 B1 | 11/1984 |
| EP | 0 197 718 B1 | 10/1986 |
| EP | 0 212 959 B1 | 3/1987 |
| EP | 0 219 208 B1 | 4/1987 |

(List continued on next page.)

OTHER PUBLICATIONS

Bauer et al., "Modification of Growth Related Enzymatic Pathways and Apparent Loss of Tumorigenicity of a ras–transformed Bovine Endothelial Cell Line by Treatment with 5–Iodo–6–amino–1,2–benzopyrone (INH$_2$BP)", *Intl. J. Oncol.*, 8:239–52 (1996).

Cosi et al., "Poly(ADP–Ribose) Polymerase (PARP) Revisited. A New Role for an Old Enzyme: PARP Involvement in Neurodegeneration and PARP Inhibitors as Possible Neuroprotective Agents", *Ann. N. Y. Acad. Sci.*, 825:366–79 (1997).

Cosi et al., "Poly(ADP–Ribose) Polymerase Inhibitors Protect Against MPTP–induced Depletions on Striatal Dopamine and Cortical Noradrenaline in C57B1/6 Mice", *Brain Res.*, 729:264–69 (1996).

Cristovao et al., "Effect of a Poly(ADP–Ribose)Polymerase Inhibitor on DNA Breakage and Cytotoxicity Induced by Hydrogen Peroxide and γ–Radiation", *Terato., Carcino., and Muta.*, 16:219–27 (1996).

Cuzzocrea, "Role of Peroxynitrite and Activation of Poly(ADP–Ribose) Synthetase in the Vascular Failure Induced by Zymosan–activated Plasma", *Brit. J. Pharm.*, 122:493–503 (1997).

Endres et al., "Ischemic Brain Injury is Mediated by the Activation of Poly(ADP–Ribose) Polymerase," *J. Cerebral Flood Flow Metabol.*, 17(11):1143–51 (1997).

Heller et al., "Inactivation of the Poly(ADP–Ribose)Polymerase Gene Affects Oxygen Radical and Nitric Oxide Toxicity in Islet Cells", *J. Biol. Chem.*, 270:11176–80 (1995).

(List continued on next page.)

Primary Examiner—Mukund J. Shah
Assistant Examiner—Tamthom N. Truong
(74) Attorney, Agent, or Firm—Nixon & Vanderhye P.C.

(57) ABSTRACT

Poly(ADP-ribose) polymerase ("PARP") inhibitors and methods for treating neurodegenerative diseases, neural tissue damage related to cerebral ischemia and reperfusion injury, and cardiovascular in an animal.

19 Claims, No Drawings

U.S. PATENT DOCUMENTS

| | | | |
|---|---|---|---|
| 3,700,673 A | 10/1972 | Watson | 260/287 |
| 3,719,684 A | 3/1973 | Unger et al. | 260/294.8 |
| 3,759,924 A | 9/1973 | Jeanmart et al. | 260/286 |
| 3,830,816 A | 8/1974 | Gittos et al. | 260/286 |
| 3,838,134 A | 9/1974 | Glauthier | 260/286 |
| 3,899,529 A | 8/1975 | Witzel | 260/517 |
| 3,900,477 A | 8/1975 | Philipp et al. | 260/288 |
| 3,904,671 A | 9/1975 | Minatoya | 260/473 |
| 3,932,643 A | 1/1976 | Gauthier | 424/258 |
| 3,950,343 A | 4/1976 | Philipp et al. | 260/288 |
| 3,978,066 A | 8/1976 | Philipp et al. | 260/288 |
| 3,991,064 A | 11/1976 | Brown et al. | 260/288 |
| 4,031,097 A | 6/1977 | Bach et al. | 260/285.5 |
| 4,082,741 A | 4/1978 | Hunger et al. | 260/154 |
| 4,169,897 A | 10/1979 | Meyer et al. | 424/330 |
| 4,218,453 A | 8/1980 | Hannart | 424/256 |
| 4,309,543 A | 1/1982 | Keeley | 546/76 |
| 4,382,943 A | 5/1983 | Winter et al. | 424/267 |
| RE31,617 E | 6/1984 | Beverung, Jr. et al. | 544/250 |
| 4,472,401 A | 9/1984 | Kennewell et al. | 424/251 |
| 4,594,415 A | 6/1986 | Robins et al. | 536/27 |
| 4,639,454 A | 1/1987 | Hesson | 514/259 |
| 4,740,581 A | 4/1988 | Pruett et al. | 528/289 |
| 4,742,171 A | 5/1988 | Martin et al. | 546/81 |
| 4,902,695 A | 2/1990 | Ornstein | 514/307 |
| 4,902,798 A | 2/1990 | Nakamatsu et al. | 546/76 |
| 4,925,968 A | 5/1990 | Sestanj et al. | 560/21 |
| 5,032,617 A | 7/1991 | Lee et al. | 564/74 |
| 5,041,653 A | 8/1991 | Lee et al. | 564/74 |
| 5,077,035 A | 12/1991 | Wieland et al. | 424/1.1 |
| 5,177,075 A | 1/1993 | Suto et al. | 514/248 |
| 5,215,738 A | 6/1993 | Lee et al. | 424/10 |
| 5,262,564 A | 11/1993 | Schohe et al. | 562/430 |
| 5,274,097 A | 12/1993 | Schohe et al. | 546/208 |
| 5,338,851 A | 8/1994 | Huff et al. | 546/141 |
| 5,391,376 A | 2/1995 | Long, Jr. et al. | 424/450 |
| 5,395,835 A | 3/1995 | Glase et al. | 514/254 |
| 5,414,001 A | 5/1995 | Ireland et al. | 514/287 |
| 5,420,136 A | 5/1995 | Lewis et al. | 514/296 |
| 5,434,188 A | 7/1995 | Boschelli et al. | 514/617 |
| 5,464,871 A | 11/1995 | Kun et al. | 514/617 |
| 5,473,074 A | 12/1995 | Kun et al. | 546/141 |
| 5,480,631 A | 1/1996 | De Paulis et al. | 424/185 |
| 5,482,975 A | 1/1996 | Kun et al. | 514/619 |
| 5,516,941 A | 5/1996 | Kun et al. | 564/166 |
| 5,587,384 A | 12/1996 | Zhang et al. | 514/309 |
| 5,589,483 A | 12/1996 | West | 514/310 |
| 5,618,813 A | 4/1997 | Chu et al. | 514/233.2 |
| 5,633,282 A | 5/1997 | Collins et al. | 514/622 |
| 5,635,506 A * | 6/1997 | Alberts et al. | 514/232.8 |
| 5,652,260 A | 7/1997 | Kun et al. | 514/457 |
| 5,652,367 A | 7/1997 | Kun et al. | 546/141 |
| 5,656,638 A | 8/1997 | Gaeta et al. | 514/301 |
| 5,659,082 A | 8/1997 | Flitter et al. | 564/166 |
| 5,665,710 A | 9/1997 | Rahman et al. | 514/44 |
| 5,670,518 A | 9/1997 | Kun et al. | 514/309 |
| 5,703,089 A | 12/1997 | Braña et al. | 514/284 |
| 5,703,116 A | 12/1997 | Gaeta et al. | 514/443 |
| 5,719,151 A | 2/1998 | Shall et al. | 514/248 |
| 5,753,674 A | 5/1998 | Kun et al. | 514/309 |
| 5,756,510 A | 5/1998 | Griffin et al. | 514/261 |
| 5,760,062 A | 6/1998 | Gaeta et al. | 514/344 |
| 5,767,135 A | 6/1998 | Fernandez-Pol | 514/354 |
| RE36,397 E | 11/1999 | Zhang et al. | 514/309 |
| 6,121,278 A | 9/2000 | Li et al. | |
| 6,197,785 B1 | 3/2001 | Jackson | 514/309 |
| 6,201,020 B1 | 3/2001 | Zhang | 514/544 |
| 6,235,748 B1 | 5/2001 | Li | 514/285 |

FOREIGN PATENT DOCUMENTS

| | | |
|---|---|---|
| EP | 0 355 750 | 2/1990 |
| EP | 0 555 750 | 2/1990 |
| EP | 0 393 926 | 10/1990 |
| EP | 393926 | 10/1990 |
| EP | 0 539 805 | 5/1993 |
| EP | 0 638 309 A1 | 2/1995 |
| EP | 0676 201 | 10/1995 |
| FR | 1199252 | 12/1957 |
| FR | 7 723 M | 3/1970 |
| FR | 2 205 333 | 5/1974 |
| FR | 2 305 182 | 10/1976 |
| GB | 810108 | 3/1959 |
| GB | 838994 | 6/1960 |
| GB | 1263044 | 2/1972 |
| GB | 1379111 | 1/1975 |
| GB | 1474775 | 5/1977 |
| GB | 1545767 | 5/1979 |
| JP | 3-205402 | 9/1991 |
| JP | 032 05402 A2 | 9/1991 |
| JP | 4-13684 | 1/1992 |
| JP | 040 13684 A2 | 1/1992 |
| JP | 042 75223 A2 | 9/1992 |
| JP | 4-275223 | 9/1992 |
| JP | 042 75296 A2 | 9/1992 |
| JP | 4-275296 | 9/1992 |
| WO | WO 90/07502 | 7/1990 |
| WO | WO 92/00281 | 1/1992 |
| WO | WO 92/05770 | 4/1992 |
| WO | WO 92/15266 | 9/1992 |
| WO | WO 93/05096 | 3/1993 |
| WO | WO 93/18748 | 9/1993 |
| WO | WO 95/04720 | 2/1995 |
| WO | WO 95/24379 | 9/1995 |
| WO | WO 95/29895 | 11/1995 |
| WO | WO 95/30409 | 11/1995 |
| WO | WO 96/28167 | 9/1996 |
| WO | WO 96/33268 | 10/1996 |
| WO | WO 97/30054 | 8/1997 |
| WO | WO 97/38977 | 10/1997 |
| WO | WO 98/27975 | 7/1998 |
| WO | WO 99/11622 | 3/1999 |
| WO | WO 99/11623 | 3/1999 |
| WO | WO 99/11624 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/59973 | 11/1999 |
| WO | WO 99/59975 | 11/1999 |
| WO | WO 00/39070 | 7/2000 |
| WO | WO 00/39104 | 7/2000 |

OTHER PUBLICATIONS

Hughes et al., "Induction of T Helper Cell Hyporesponsiveness in an Experimental Model of Autoimmunity by Using Nonmitogenic Anti–CD3 Monoclonal Antibody", *J. Immuno.*, 153:3319–25 (1994).

Salzman et al., "Role of Peroxynitrite and Poly(ADP–Ribose) Synthase Activation Experimental Colitis", *Japanese J. Pharm.*, 75, Supp. I:15 (1997).

Southan et al., "Spontaneous Rearrangement of Aminoalkylisothioureas into Mercaptoalkylguanidines, a Novel Class of Nitric Oxide Synthase Inhibitors with Selectivity Towards the Inducible Isoform", *Br. J. Pharm.*, 117:619–32 (1996).

Szabó et al., "Mercaptoethylguanidine and Guanidine Inhibitors of Nitric Oxide Synthase React with Peroxynitrite and Protect Against Peroxynitrite–induced Oxidative Damage", *J. Biol. Chem.*, 272:9030–36 (1997).

Szabó et al., "Protective Effects on an Inhibitor of Poly(ADP–Ribose) Synthetase in Collagen–Induced Arthritis," *Japanese J. Pharm.*, 75, Supp. I:1–2 (1997).

Szabó et al., "DNA Strand Breakage, Activation of Poly-(ADP–Ribose) Synthetase, and Cellular Energy Depletion are Involved in the Cytotoxicity in Macrophages and Smooth Muscle Cells Exposed to Peroxynitrite", *Proc. Natl. Acad. Sci. USA,* 93:1753–58 (1996).

Wallis, et al., Traumatic Neuroprotection with Inhibitors of Nitric Oxide and ADP–Ribosylation, *Brain Res.,* 710:169–77 (1996).

Weltin et al., "Effect of 6(5H)–Phenanthridinone, an Inhibitor of Poly(ADP–ribose) Polymerase, on Cultured Tumor Cells", *Oncol. Res.,* 6:399–403 (1994).

Zingarelli et al., "Protective Effects of Nicotinamide Against Nitric Oxide–Mediated Delayed Vascular Failure in Endotoxic Shock: Potential Involvement of PolyADP Ribosyl Synthetase", *Shock,* 5:258–64 (1996).

Zhang et al., "Nitric Oxide Activation of Poly(ADP–Ribose) Synthetase in Neurotoxicity", *Science,* 263:687–89 (1994).

Wallis et al., "Neuroprotection Against Nitric Oxide Injury with Inhibitors of ADP–Ribosylation", *NeuroReport,* 5:3, 245–48 (1993).

Banasik et al., "Specific Inhibitors of Poly(ADP–Ribose) Synthetase and Mono(ADP–Ribosyl)transferease", *J. of Biol. Chem.,* 267:3, 1569–75 (1992).

Banasik et al., "Inhibitors and Activators of ADP–Ribosylation Reactions", *Molec. and Cell. Biochem.,* 138:185–97 (1994).

Thiemermann et al., "Inhibition of the Activity of Poly(ADP Ribose) Synthetase Reduces Ischemia–Reperfusion Injury in the Heart and Skeletal Muscle", *Proc. Natl. Acad. Sci. USA,* 94:679–83 (1997).

Zhang et al., "Poly(ADP–Ribose) Synthetase Activation: An Early Indicator of Neurotoxic DNA Damage", *J. of Neurochem.,* 65:3, 1411–14 (1995).

Dawson et al., "Protection of the Brain from Ischemia", *Cerebrovascular Disease,* 319–25 (Batjer ed. 1997).

Dawson et al., "Nitric Oxide Mediates Glutamate Neurotoxicity in Primary Cortical Cultures", *Proc. Natl. Acad. Sci. USA,* 88:6368–71 (1991).

Dawson et al., "Mechanisms of Nitric Oxide–mediated Neurotoxicity in Primary Brain Cultures", *J. Neurosci.,* 13:6, 2651–61 (1993).

Dawson et al., "Resistance to Neurotoxicity in Cortical Cultures from Neuronal Nitric Oxide Synthase–Deficient Mice," *J. Neurosci.,* 16:2479–87 (1996).

Iadecola, "Bright and Dark Sides of Nitric Oxide in Ischemic Brain Injury", *Trends Neurosci.,* 20:3, 132–39 (1997).

Huang et al., "Effects Of Cerebral Ischemia in Mice Deficient in Neuronal Nitric Oxide Synthase", *Science,* 265:1883–85 (1994).

Beckman et al., "Pathological Implications of Nitric Oxide, Superoxide and Peroxynitrite Formation", *Biochem. Soc. Trans.,* 21:330–34 (1993).

Milam et al., "Inhibitors of Poly(Adenosine Diphosphate–Ribose) Synthesis: Effect on Other Metabolic Processes," *Science,* 223:589–91 (1984).

Desilets et al., "Design and Synthesis of Near–Infrared Absorbing Pigments", *Can. J. Chem.,* 73:319–35 (1995). (Part I and Part II).

Langlois et al., "Synthesis of Quinazoline–2, 4–dione and Naphthalimide Derivatives as New 5–HT$_3$ Receptor Antagonists", *Eur. J. Med. Chem.,* 29:925–40 (1994).

Nowicki et al., "Nitric Oxide Mediates Neuronal Death After Focal Cerebral Ischemia in the Mouse", *Eur. J. Pharm.,* 204:339–40 (1991).

Purnell et al. "Novel Inhibitors of Poly(ADP–Ribose) Synthetase", *Biochem. J.,* 185:775–77 (1980).

Suto et al., "Dihydroisoquinolines: The Design and Synthesis of a New Series of Potent Inhibitors of Poly(ADP–Ribose) Polymerase", *Anti–Cancer Drug Design,* 7:107–17 (1991).

Baddar, Chemical Abstract, vol. 81:37417, 1974.

Baddar, Chemical Abstract, vol. 83:27978, 1975.

Beilstein Handbook of Organic Chemistry, Reg. No. 13823, 1999.

Beilstein Handbook of Organic Chemistry, Reg. No. 56052, 1998.

Beilstein Handbook of Organic Chemistry, Reg. No. 207516, 1998.

Beilstein Handbook of Organic Chemistry, Reg. No. 207532, 1998.

Beilstein Handbook of Organic Chemistry, Reg. No. 222316, 1998.

Beilstein Handbook of Organic Chemistry, Reg. No. 244756, 1998.

Beilstein Handbook of Organic Chemistry, Reg. No. 245245, 1998.

Beilstein Handbook of Organic Chemistry, Reg. No. 254129, 1998.

Beilstein Handbook of Organic Chemistry, Reg. No. 332938, 1998.

Cabares, Chemical Abstract, vol. 92:198336, 1980.

Cabares, Chemical Abstract, vol. 107:23262, 1987.

Campbell, Chemical Abstract, vol. 54, 22647, 1961.

Campbell, Chemical Abstract, vol. 75:98422, 1971.

Cookson, Chemical Abstract, vol. 84:4857.

Crossland, Chemical Abstract, vol. 64:3526h, 1966.

Dokunikhin, Chemical Abstract, vol. 59:10037, 1963.

Dokunikhin, Chemical Abstract, vol. 61:9493, 1964.

Duval, Chemical Abstract, vol. 108:21627, 1988.

Gomes, Chemical Abstract, vol. 93:26178, 1980.

Griffin et al., "The role of poly(ADP–ribose) polymerase as resistance–modifying agents in cancer therapy", Biochimie vol. 77 No. 6, pp. 408–22 (1995).

Harris, "DNA repair: relationship to drug and radiation resistance, metastasis and growth factors", Int. J. Radiat. Biol. Relat. Stud. Phys. Chem. Med. vol. 48 No. 5, pp. 675–690 (1985).

Hofer, Chemical Abstract vol. 69:87767, 1968.

Hofer, Chemical Abstract vol. 70:115926, 1969.

Houlihan, Chemical Abstract, vol. 87:152015, 1977.

Houlihan, Chemical Abstract, vol. 95:168911, 1981.

Humber, Chemical Abstract, vol. 86:171282, 1977.

Kametani, Chemical Abstract, vol. 65:15319, 1966.

Krepelka, Chemical Abstract, vol. 97:38635, 1982.

Kuehn, Chemical Abstract, vol. 62:9129, 1965.

Lam, "The effect of 3–aminobenzamide, an inhibitor of poly–ADP–ribose polymerase, on ischemia/reperfusion damage in rat retina", Res. Comm. Mol. Pathol. Pharmacol. vol. 95 No. 3, pp. 241–252 (Mar. 1997).

Mao et al., "The inhibition of nitric oxide–activated poly-(ADP–ribose) synthetase attenuates transsynaptic alternation of spinal cord dorsal horn neurons and neuropathic pain in the rat", Pain vol. 72, pp. 355–366 (1997).

Mavoungou–Gomes, Chemical Abstract, vol. 74:111797, 1971.

Mavoungou–Gomes, Chemical Abstract, vol. 76:85774, 1972.

Mavoungou–Gomes, Chemical Abstract, vol. 82:170471, 1975.

Mavoungou–Gomes, Chemical Abstract, vol. 90:38734, 1979.

Oleinik, Chemical Abstract, vol. 100:139054, 1984.

Paaphorst & E.I. Azzam, "Poly–ADP–ribose synthetase inhibitors increase radiation and thermal sensitivity but do not effect thermotolerance", Radiat. Res. vol. 116 No. 3, pp. 442–452 (1988).

Perrin, Chemical Abstract, vol. 63:7006, 1965.

Quelet, Chemical Abstract, vol. 61:13305, 1964.

Richter, Chemical Abstract, vol. 124:131261, 1995.

Rodway, Chemical Abstract, vol. 76:14566, 1972.

Rodway, Chemical Abstract, vol. 82:171011, 1975.

Rokach, Chemical Abstract, vol. 92:146482, 1980.

Ruf et al., "Structure of the catalytic fragment of poly(ADP–ribose) polymerase from chicken", Proc. Natl. Acad. Sci. USA vol. 93, pp. 7481–7485 (Jul. 1996).

Schmidt–Nickels, Chemical Abstract, vol. 52:5846, 1958.

Sieglitz, Chemical Abstract, vol. 58:7884, 1963.

Sklar et al., "Combined antitumor effect of suramin plus irradiation in human prostate cancer cells: the role of apoptosis", J. Urol. vol. 150, pp. 1526–1532 (Nov. 1993).

Van Gool et al., "Overexpression of human poly(ADP–ribose) polymerase in transfected hamster cells leads to increased poly(ADP–ribosyl)ation and cellular sensitization to □ irradiation", Eur. J. Biochem. vol. 244, pp. 15–20 (1997).

Vaziri et al., "ATM–dependent telomere loss in aging human diploid fibroblasts and DNA damage lead to the post–translational activation of p53 protein involving poly(ADP–ribose) polymerase", The EMBO Journal vol. 16 No. 19, pp. 6018–6033 (1997).

Weltin et al., "Effect of 6(5H)–phenanthridinone, a poly(ADP–ribose)polymerase inhibitor, and ionizing radiation of the growth of cultured lymphoma cells", Int. J. Radiat. Biol. vol. 72 No. 6, pp. 685–692 (Dec. 1997).

Zaitsev, Chemical Abstract, vol. 84:3986, 1976.

Zaitsev, Chemical Abstract, vol. 84:42754, 1976.

Zinchenko, Chemical Abstract, vol. 77:61927, 1972.

Mandir et al. (PNAS 96: 5774–5779 (May 1999).

Cosi et al. (Brain Research 809 (1998) 58–67).

Love et al. (Brain (1999) 122, 247–253).

Rhun et al. (Biochemical and Biophysical Research Communications 245, 1–10 (1998)).

Zhang et al (Biochemical and Biophysical Research Communications 278, 590–598 (2000)).

McConnel et al.; J.Chem.Soc.; 1956; 812.

Chiba, Koji; Tagaya, Hideyuki; Karasu, Masa; Ono, Tsuyoyuki; Kugiya, Masashi; Chem.Lett.; EN; 1990; 39–42.

Gootjes et al.; J.Med.Pharm.Chem.; 3; 1961; 157, 159.

Oleinick et al, Radiation Research 101, 29–46, 1985).

Arnett, Edward M.; Flowers, Robert A.; Ludwig, Richard T.; Meekhof, Alison E.; Walek, Stuart A. J.Phys.Org.Chem.; EN; 10; 7; 1997; 499–513.

Dokunichin, Beilstein Handbook of Organic Chem., Reg. No. 618403, 1988.

Dokunichin, Beilstein Handbook of Organic Chem., Reg. No. 827161, 1988.

Dokunichin, Beilstein Handbook of Organic Chem., Reg. No. 821484, 1988.

Dokunichin, Beilstein Handbook of Organic Chem., Reg. No. 619108, 1988.

Dokunichin, Beilstein Handbook of Organic Chem., Reg. No. 657772, 1988.

Dokunichin, Beilstein Handbook of Organic Chem., Reg. No. 653888, 1988.

Oleinik, Beilstein Handbook of Organic Chem., Reg. No. 4483194, 1991.

Oleinik, Beilstein Handbook of Organic Chem., Reg. No. 4494786, 1991.

Sielitz, Beilstein Handbook of Organic Chem., Reg. No. 807933, 1988.

Dokunichin, Beilstein Handbook of Organic Chem., Reg. No. 746893, 1988.

Gomes, Beilstein Handbook of Organic Chem., Reg. No. 656117, 1988.

Rokach, Beilstein Handbook of Organic Chem., Reg. No. 1571164, 1988.

Humber et al., Beilstein Handbook of Organic Chem., Reg. No. 1541605, 1988.

Mavoungou Gomes, Beilstein Handbook of Organic Chem., Reg. No. 751834, 1988.

Mavoungou Gomes, Beilstein Handbook of Organic Chem., Reg. No. 670954, 1988.

Dokunichin, Beilstein Handbook of Organic Chem., Reg. No. 649696, 1988.

Dokunichin, Beilstein Handbook of Organic Chem., Reg. No. 660681, 1988.

Dokunichin, Beilstein Handbook of Organic Chem., Reg. No. 530731, 1988.

Beilstein Handbook of Organic Chem. Reg. No. 3140506 1998.

Beilstein Handbook of Organic Chem. Reg. No. 165349 1998.

Beilstein Handbook of Organic Chem. Reg. 161148 1998.

Beilstein Handbook of Organic Chem. Reg. No. 2213597 1999.

Biochemical and Biophysical Research Communications 136(3), 1110–15 1986 Tanuma et al.

Biochemical and Biophysical Research Communications 195, No. 2, 558–564 1993 Jesser et al.

Biochemical and Biophysical Research Communication 195(2), 558–64 1993 Jesser et al.

Biochemical and Biophysical Research Communications 210, No. 2, 329–337 1995 Aoki et al.

Biochemical and Biophysical Research Communications 220, 411–17 1996 Uchiumi et al.

Biochemical and Biophysical Research Communications 236, 265–69 1997 Maruta et al.

Biochemical Society Transactions vol. 8(2), 192–193 1980 Whitby et al.

Biochemistry 30, 5907–5912 1991 Maruta et al.

Biochemistry International 16, No. 3, 397–403 1988 Concha et al.

Biochemistry International 19, No. 6, 1395–1402 1989 Tanuma et al.

Biochemistry International 18, No. 4, 701–708 1989 Tanuma et al.

Biochemistry International 24, No. 5, 889–897 1991 Tsai et al.
Biochimica et Biophysica Acta 827, 228–234 1985 Tavassoli et al.
Biochimica et Biophysica Actas 1158, 251–56 1993 Aoki et al.
Bull. Chem. Soc. Jpn. 61(6):2238–40 1988 Sato et al.
Bull. Soc. Chim. Fr. 233 1962 Granger et al.
C. R. Acad. Sci. 275:17, 961–64 1972 Michailidis et al.
Cell 94, 325–337 1998 Kuida et al.
Cell 94, 339–352 1998 Hakem et al.
Cell Biology and Toxicology 9, No. 2, 165–175 1993 Clayson et al.
Chem Abstracts 52:17 (14606h) (Sep. 10) 1958 Ochiai et al.
Chem Abstracts 55:6 (5491ce) (Mar. 20) 1961 Ochiai et al.
Chem Abstracts 58:4 (3425d) (Feb. 18) 1963 Hayashi et al.
Chem Abstracts vol. 126, No. 17, 229493f Apr. 28 1997 Angeliki.
Chem. Abstracts 64:695e 1966 Ried et al.
Chem. Ber. 46,pp. 2087, 2089 1913 Kardos.
Chemical Abstract 54:22648a Nikitskaya et al.
Chemical Abstract vol. 51:1960 1957 Taylor et al.
Chemical Abstract vol. 52:6285 1958 Ohta.
Chemical Abstract vol. 52:4646 1958 Gilman et al.
Chemical Abstract vol. 52:5846b 1958 Gateff et al.
Chemical Abstract vol. 55:12868a 1961.
Chemical Abstract vol. 55:12868b 1961.
Chemical Abstract vol. 55:12868c 1961.
Chemical Abstract vol. 59:10037c 1963 Hazard et al.
Chemical Abstract vol. 61:15194 1964 Tsuboi.
Chemical Abstract vol. 61:9494a 1964 Dokunikhin et al.
Chemical Abstract vol. 61:9493f 1964 Bodea et al.
Chemcial Abstract vol. 61:13305g 1964 Badger et al.
Chemical Abstract vol. 62:5259 1965 Lakeside Lab., Inc.
Chemical Abstract vol. 63:4256 1965 Keene et al.
Chemical Abstract vol. 62:9129g 1965 Klosa.
Chemical Abstract vol. 65:15320a 1966 Kametani.
Chemical Abstract vol. 65:15319h 1966 Humber et al.
Chemical Abstract vol. 68:59420 1968 Chandler et al.
Chemical Abstract vol. 70:3629 1969 Weis.
Chemical Abstract vol. 70:67988 1969 Resplandy et al.
Chemical Abstract vol. 70:4079 1969 Coyne et al.
Chemical Abstract vol. 73:35200 1970 Pan et al.
Chemical Abstract vol. 72:121337 1970 Pan et al.
Chemical Abstract 74:110112y (p. 252 May 10) 1971 Damas.
Chemical Abstract vol. 78:123624 1973 Swenton et al.
Chemical Abstract vol. 78:68700 1973 Roehm et al.
Chemical Abstract vol. 78:58193 1973 Mondon et al.
Chemical Abstract vol. 78:84227 1973 Kraatz et al.
Chemical Abstract vol. 78:29384 1973 Forrester et al.
Chemical Abstract vol. 78:29593 1973 Cerbai et al.
Chemical Abstract vol. 81:37489 1974 Cerbai et al.
Chemical Abstract vol. 85:182 1976 Tullar et al.
Chemical Abstract vol. 84:16943 1976 Minatoya et al.
Chemical Abstract vol. 85:77216 1976 Ege et al.
Chemcial Abstract 85(1976)159898a 1976.
Chemical Abstract vol. 87:5778 1977 Fomenko et al.
Chemical Abstract vol. 82:30602 1978 Minatoya et al.
Chemical Abstract vol. 90:6486t 1979 Takahashi.
Chemical Abstract vol. 91:39035 1979 Migachev.
Chemical Abstract vol. 92:181104e 1980 Ryabukhina et al.
Chemical Abstract vol. 92:41620 1980 Migachev et al.
Chemical Abstract vol. 92:41511 1980 Migachev et al.

Chemical Abstract 92:22393 1980 Simmonds.
Chemical Abstract vol. 95:80661 1981 Narasimhan et al.
Chemical Abstract vol. 95 (9):80666 1981 Migachev et al.
Chemcial Abstract vol. 95:80688 1981 Migachev et al.
Chemical Abstract vol. 95:42867 1981 Migachev et al.
Chemical Abstract vol. 95:42866 1981 Migachev et al.
Chemical Abstract vol. 95:187120 1981 Migachev et al.
Chemical Abstract vol. 96:6539m, p.592 1982 Singh et al.
Chemical Abstract vol. 96:68519 1982 Leardini et al.
Chemical Abstract vol. 97:126680 1982 Grimshaw et al.
Chemical Abstract vol. 100:103453 1984 Prostakov et al.
Chemical Abstract vol. 100:191713 1984 Orlic–Nuber et al.
Chemical Abstract vol. 102:203854 1985 Migachev et al.
Chemical Abstract vol. 105:60505 1986 Andrievskii et al.
Chemical Abstract vol. 106 (67553) 1987 Pellefier.
Chemical Abstract vol. 107:39655v 1987 Bondarenko et al.
Chemical Abstract vol. 110:230971 1989 Val'kova et al.
Chemical Abstract vol. 113:190649 1990 Val'Kova et al.
Chemical Abstract vol. 112:44716 1990 Korol'kova et al.
Chemical Abstract vol. 112:128235 1990 Korol'kova et al.
Chemical Abstract vol. 112:216749 1990 Benson et al.
Chemical Abstract vol. 114: 143456 1991 Walser.
Chemical Abstract vol. 115 (232107) 1991 Nagao.
Chemical Abstract vol. 115:70731f 1991 Donshikh et al.
Chemical Abstract vol. 115:158338 1991 Buckman et al.
Chemical Abstract vol. 114:42543 1991 Andrievskii et al.
Chemical Abstract vol. 119:72127 1993 Zaitsev et al.
Chemical Abstract vol. 118:191567 1993 Dow.
Chemical Abstract vol. 118:80722 1993 Dininno et al.
Chemical Abstract vol. 118:101709 1993 Dininno et al.
Chemical Abstract vol. 120:134231 1994 Rocca et al.
Chemical Abstract vol. 121:220651v 1994 Pawlowska et al.
Chemical Abstract vol. 121:172572 1994 Liu et al.
Chemical Abstract vol. 120:95793 1994 Kyota et al.
Chemical Abstract vol. 121:57315 1994 Dow et al.
Chemical Abstract vol. 120:148508p 1994 Barros et al.
Chemical Abstract vol. 123:505 1995 Weltin et al.
Chemical Abstract vol. 122:10865 1995 Lamba et al.
Chemical Abstract vol. 122:170499 1995 Korol'kova et al.
Chemical Abstract vol. 123:256711 1995 Kalindjian et al.
Chemical Abstract vol. 122:170250 1995 Gorio et al.
Chemical Abstract vol. 122:187249 1995 Dininno et al.
Chemical Abstract 122:316902 1995 Desilets et al.
Chemical Abstract 122:316901 1995 Desilets et al.
Chemical Abstract 122:187526 1995 Langlois et al.
Chemical Abstract vol. 125:87882 1996 Yamaguchi et al.
Chemical Abstract vol. 124:331706 1996 Silverman et al.
Chemical Abstract vol. 126:115554 1996 Malhotra et al.
Chemical Abstract vol. 125:246943 1996 Korol'kova et al.
Chemical Abstract vol. 125:277462 1996 Ge et al.
Chemical Abstract 124:202047 1996 Fernandez et al.
Chemical Abstract vol. 128:36109 1997 Sakai et al.
Chemical Abstract vol. 127:234258 1997 Reddy et al.
Chemical Abstract vol. 127:81282 1997 Marek et al.
Chemical Abstract vol. 128:34752 1997 Jones et al.
Chemical Abstract vol. 127:80243 1997 Banister et al.
Chemical Abstract abstract no. 17462 1998 Yoshida et al.
Chemical Abstract vol. 129:104224 1998 West.
Chemical Abstract vol. 128:138099 1998 Weltin et al.
Chemical Abstract vol. 130:24816 1998 Park et al.
Chemical Abstract vol. 128:75320 1998 Jones et al.
Chemical Abstract vol. 128:165850 1998 Cookson et al.
Chemical Abstract vol. 129:54301 1998 Albright et al.
Itsu Kenkusho Nempo 16:15–23 1971 Ochiai et al.

J. Chem. Soc. 11:1293–97 1978 Davies et al.
J. Am. Chem. Soc. 78:5104–8 1956 Taylor et al.
J. Biol. Chem. 246(20), 6362–64 1972 Miwa et al.
J. Biol. Chem. 261(32), 14902–11 1986 Hatakeyama et al.
J. Biol. Chem. 262(36), 17641–50 1987 Ikejima et al.
J. Biol. Chem. 263(23), 11037–40 1988 Ikejima et al.
J. Biol. Chem. 267(20), 14436–42 1992 Tsai et al.
J. Chem Soc. 12:2231–2241 1971 Barton.
J. Chem. Res., Synop. 8:302 1995 Mueller et al.
J. Chem. Res., Synop. 2:126 1996 Mueller et al.
J. Chem. Soc. pp. 1979–1984 1929 Blount et al.
J. Chem. Soc. 1624–28 1958 Johnson.
J. Chem. Soc. 4295–98 1962 Brown et al.
J. Chem. Soc. 1:14, 1747–51 1974 Ninomiya et al.
J. Chem. Soc. 1:7, 763–70 1974 Bailey et al.
J. Exp Med. vol. 186, No. 7, Oct. 6, 1997, 1041–9, 1997 Szabo.
J. Het. Chem vol. 7, pp. 597–605 1970 Pan et al.
J. Heterocycl. Chem. 20:5, 1407–9 1983 Rougeot et al.
J. Med. Chem. 38, 389–393 1995 Slama et al.
J. Med. Chem. 38, 4332–4336 1995 Slama et al.
J. Neuroscience Res. 47:372–383 1997 Ceruti et al.
J. of Biological Chemistry 261(2), 965–69 1986 Tanuma et al.
J. Org Chem. 29:3, 681–85 1964 Masamune et al.
J. Org Chem. 47, 2043–2047 1982 Taylor et al.
J. Org. Chem. vol. 23, pp. 1071–2 Jul. 1956 Robinson et al.
J. Org. Chem. 29:11, 3180–85 1964 Baer et al.
J. Org. Chem. 43:11, 2190–96 1978 Eisch et al.
JACS 71:937–8 (Mar.) 1949 Wilson et al.
JACS 76:4396–8 (Sep. 5) 1954 Wright.
JCS pp. 4067–75 1952 Peak et al.
JCS pp. 1294–1304 1956 Albert et al.
JCS pp. 2384–2396 1959 Albert et al.
Journal of Cellular Biochemistry 29:361–372 1985 Bolander, Jr.
Journal of Cerebral Blood Flow and Metabolism 17 No. 11, 1137–1142 1997 Takahashi et al.
Journal of Heterocyclic Chemistry vol. 3, pp. 466–469 Dec. 1966 Aparajithan.
Journal of Heterocyclic Chemistry vol. 15, pp. 1513–1514 1978 Nuvole et al.
Journal of Medicinal Chemistry vol. 20 (3) 449–452 1977 Diana et al.
Journal of Neurochemistry 70, No. 2, 501–508 1998 Cookson et al.
Journal of Organic Chemistry vol. 11, No. 3, 239–246 1946 Bergstrom et al.
Journal of Organic Chemistry 53(20):4650–3 1988 D. Dumas.
Journal of the Chemical Society pp. 1799–1803 1972 Singh et al.
Journal of the Chemical Society vol. 9, 944–950 1976 Loewenthal et al.
Justus Liebigs Ann. Chem. 388, p. 212 1912 Ullmann et al.
Med Chem. Res. 6:2, 81–101 1996 Castan et al.
Mutation Research 218, 67–74 1989 Gonzalez et al.
Mutation Research 350, 25–34 1996 Wachsman.
Nature Medicine JHU 1997 Eliasson et al.
Neuron 1, 623–634 1988 Choi.
Pharm. Bull. 5:289–91 1957 Ochiai et al.
Phosphorus Sulfur vol. 14, No. 1, pp. 131–8 1983 Becher et al.
Ric. Sci. 38:3, 231–33 1968 Di Maio et al.
Rocz. Chem. 41:1,89–101 1967 Schoen et al.
Science 282, 1484–1487 1998 Smith et al.
Spin Label Analogue of ATP 246, No. 20, 6362–6364 1971 Miwa et al.
Switzerland Patent 601 246 1978.
Tetrahedro supp. 8, part 1, pp. 305–12 1966 Tamayo et al.
Tetrahedron Letter 32, No. 35, 4525–4528 1991 Chida et al.
Tetradedron Letters 36:33, 5983–86 1995 White et al.
Tetrahedron Letters 52:9, 3117–34 1996 White et al.
The Journal of Biological Chemistry 242, No. 22, 5301–5307 1967 Futai et al.
The Journal of Biological Chemistry vol. 257, No. 21, 12872–12877 1982 Wielckens et al.
The Journal of Biological Chemistry 259, No. 2, 986–995 1984 Oka et al.
The Journal of Biological Chemistry 261, No. 2, pp. 965–969 1984 Tanuma et al.
The Journal of Biological Chemisty 263, No. 23, 11037–11040 1988 Ikejima et al.
The Journal of Biological Chemisty 272, No. 18, 11895–11901 1997 Lin et al.
TiPS 11, 379–387 1990 Meldrum et al.
TIPS in press 1998 Pieper et al.
Vertex Pharmaceuticals PR Newswire 1998.

* cited by examiner

POLY(ADP-RIBOSE) POLYMERASE INHIBITORS AND METHOD FOR TREATING NEURAL OR CARDIOVASCULAR TISSUE DAMAGE USING THE SAME

BACKGROUND OF THE INVENTION

1. Field of the Invention

The invention relates to the prevention and/or treatment of neural tissue damage resulting from ischemia and reperfusion injury or other neurodegenerative diseases. More particularly, the invention concerns the prevention or treatment of vascular stroke by administering inhibitors of the nucleic enzyme poly(adenosine 5'-diphospho-ribose) synthetase ["poly(ADP-ribose) polymerase" or "PARP", which is also sometimes called "PARS" for poly(ADP-ribose) synthetase].

2. Description of the Prior Art

Poly(ADP-ribose) polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been established, this enzyme is thought to play a role in enhancing DNA repair.

During major cellular stresses, however, the extensive activation of PARP can rapidly lead to cell death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose) Synthetase in Neurotoxicity", *Science*, 263:687–89 (1994)) and in hippocampal slices (Wallis et al., "Neuroprotection Against Nitric Oxide Injury with Inhibitors of ADP-Ribosylation, *NeuroReport*, 5:3, 245–48 (1993)). The potential role of PARP inhibitors in treating neurodegenerative diseases has thus been known.

Large numbers of known PARP inhibitors have been described in Banasik et al., "Specific Inhibitors of Poly (ADP-Ribose) Synthetase and Mono(ADP-Ribosyl) transferase", *J. of Biol. Chem.*, 267:3, 1569–75 (1992), and in Banasik et al., "Inhibitors and Activators of ADP-Ribosylation Reactions", *Molec. and Cell. Biochem.*, 138:185–97 (1994).

It has been demonstrated that single injections of PARP inhibitors have reduced the infarct size caused by ischemia and reperfusion of the heart or skeletal muscle in rabbits. In these studies, a single injection of the PARP inhibitor, 3-aminobenzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", *Proc. Natl. Acad. Sci. USA*, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MPP$^+$), which participate in such pathological conditions as stroke, Alzheimer's disease and Parkinson's disease. Zhang et al., "Poly(ADP-Ribose) Synthetase Activation: An Early Indicator of Neurotoxic DNA Damage", *J. of Neurochem.*, 65:3, 1411–14 (1995).

Neural damage following stroke and other neurodegenerative processes is thought to result from a massive release of the excitatory neurotransmitter glutamate, which acts upon the N-methyl-D-aspartate (NMDA) receptors and other subtype receptors. Evidence includes findings in many animal species, as well as in cerebral cortical cultures treated with glutamate or NMDA, that glutamate receptor antagonists block neural damage following vascular stroke. Dawson et al., "Protection of the Brain from Ischemia", *Cerebrovascular Disease*, 319–325 (ed. Batjer ed. 1997).

The stimulation of NMDA receptors, in turn, activates the enzyme neuronal nitric oxide synthase (nNOS), which causes the formation of nitric oxide (NO), which more directly mediates neurotoxicity. Protection against NMDA neurotoxicity has occurred following treatment with NOS inhibitors. See Dawson et al., "Nitric Oxide Mediates Glutamate neurotoxicity in Primary Cortical Cultures", *Proc. Natl. Acad. Sci. USA*, 88:6368–71 (1991); and Dawson et al., "Mechanisms of Nitric Oxide-mediated Neurotoxicity in Primary Brain Cultures", *J. Neurosci.*, 13:6, 2651–61 (1993). Protection against NMDA neurotoxicity can also occur in cortical cultures from mice with targeted disruption of nNOS. See Dawson et al., "Resistance to Neurotoxicity in Cortical Cultures from Neuronal Nitric Oxide Synthase-Deficient Mice", *J. Neurosci.*, 16:2479–87 (1996). It is known that neural damage following vascular stroke is markedly diminished in animals treated with NOS inhibitors or in mice with nNOS gene disruption. Iaddcola, "Bright and Dark Sides of Nitric Oxide in Ischemic Brain Injury", *Trends Neurosci.*, 20:3, 132–39 (1997); and Huang et al., "Effects of Cerebral Ischemia in Mice Deficient in Neuronal Nitric Oxide Synthase", *Science*, 265:1883–85 (1994). See Beckman et al., "Pathological Implications of Nitric Oxide, Superoxide and Peroxynitrite Formation", *Biochem. Soc. Trans.*, 21:330–34 (1993). Either NO or peroxynitrite can cause DNA damage, which activates PARP.

Zhang et al., U.S. Pat. No. 5,587,384 issued Dec. 24, 1996 discusses the use of certain PARP inhibitors, such as benzamide and 1,5-dihydroxyisoquinoline, to prevent NMDA-mediated neurotoxicity and, thus, treat stroke, Alzheimer's disease, Parkinson's disease and Huntington's disease. See also, Zhang et al. "Nitric Oxide Activation of Poly(ADP-Ribose) Synthetase in Neurotoxicity", *Science*, 263:687–89 (1994).

However, the approach of using these PARP inhibitors to reduce NMDA-receptor stimulation or to treat or prevent tissue damage caused by NO is limited in effect. For example, side effects have been observed with some of the best-known PARP inhibitors, as discussed in Milam et al., "Inhibitors of Poly(Adenosine Diphosphate-Ribose) Synthesis: Effect on Other Metabolic Processes", *Science*, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose small enough to inhibit the enzyme without producing additional metabolic effects.

Certain related compounds have been disclosed for medical treatments and other uses. However, these compounds are structurally distinguishable and directed to uses which emphasize their toxic characteristics. Fernandez et al., PCT publication WO 95/29895, discloses an isoquinoline derivative which is used as an anticancer agent. Désilets et al., "Design and Synthesis of Near-Infrared Absorbing Pigments", Can J. Chem. (1995), 73: 319–335, disclose the design and synthesis of nea-infrared absorbing pigments such as aceanthrene green and derivatives. Langlois et al., "Syntheses of Quinazoline-2,4-dione and Naphthalimide Derivatives as New 5-HT$_3$ Receptor Antagonists", Eur. J. Med. Chem. (1994), 29: 925–40, disclose the preparation and 5-HT$_3$ receptor antagonist activity of certain quinazolinediones, benzisoquinolinones, and -diones. Simmonds, British Patent GB1545767 (1975) disclose benzopyranoisoquinoline derivatives useful for anti-inflammatory and central nervous system activity and also disclose a related compound useful only as an intermediate in making these distinct compounds. Kardos et al., German Patent D.R.P. 282711, disclose structurally distinct but related chlorinated compounds.

Accordingly, there remains a need for a composition containing PARP inhibitors that produce more potent and reliable effects, particularly with respect to vascular stroke.

SUMMARY OF THE INVENTION

The present invention relates to novel poly(ADP-ribose) polymerase ("PARP") inhibitors and methods for for effecting a neuronal activity in an animal using the same. The invention also relates to methods of treating and/or preventing neural tissue damage resulting from cerebral ischemia and reperfusion injury by administering the compounds of the present invention. The invention also relates to methods of treating neurodegenerative diseases and to methods of treating cardiovascular diseases in an animal by administration of the compounds of the present invention. Preferred inhibitors of poly(ADP-ribose) polymerase have an IC$_{50}$ for inhibiting poly(ADP-ribose) polymerase in vitro of 100 μM or lower. Specifically, the present invention relates to a compound of formula I:

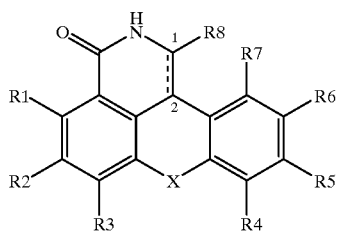

wherein
$R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$,
wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is N, O, S, or $CR_1R_2$;

with the proviso that X is not O when $R_8$ is Me or H and there is a double bond between $C_1$ and $C_2$; or a pharmaceutically acceptable salt, hydrate, or a mixture thereof.

A preferred embodiment of this invention is a compound of formula I:

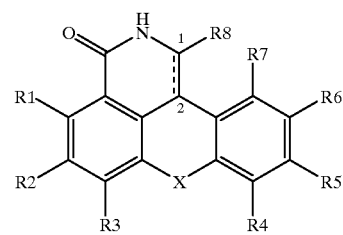

wherein $R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is N;

or a pharmaceutically acceptable salt, hydrate, or a mixture thereof.

Another preferred embodiment of this invention is a compound of formula I:

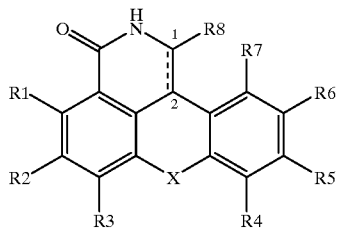

wherein $R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is S;

or a pharmaceutically acceptable salt, hydrate, or a mixture thereof.

A further embodiment of this invention is a compound of formula I:

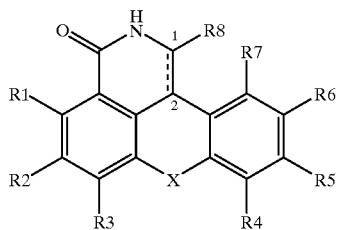

wherein $R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl; tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is $CR_1R_2$;

or a pharmaceutically acceptable salt, hydrate, or a mixture thereof.

A further embodiment of this invention is a compound of formula I:

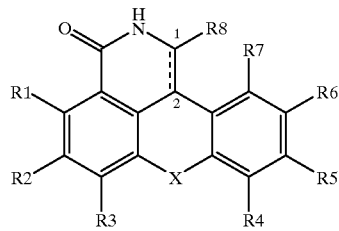

wherein $R_1$, $R_2$, $R_3$, $R_4$, $R_5$, $R_6$, $R_7$, or $R_8$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is O;

with the proviso that X is not O when $R_8$ is Me or H and there is a double bond between $C_1$ and $C_2$; or a pharmaceutically acceptable salt, hydrate, or a mixture thereof.

DETAILED DESCRIPTION OF THE INVENTION

Definitions

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Halo" means fluoro, chloro, bromo, or iodo, unless otherwise indicated.

"Phenyl" includes all possible isomeric phenyl radicals, optionally monosubstituted or multi-substituted with substituents selected from the group consisting of alkyl, alkoxy, hydroxy, halo, and haloalkyl.

The term "pharmaceutically acceptable salt" refers to salts of the subject compounds which posses the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention may possess asymmetric centers and thus can be produced as mixtures of stereoisomers or as individual stereoisomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

As used herein, the term "neural tissue damage resulting from ischemia and reperfusion injury" includes neurotoxicity, such as seen in vascular stroke and global and focal ischemia. As used herein, the term "neurodegenerative diseases," includes Alzheimer's disease, Parkinson's disease and Huntington's disease.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

What the inventors have now discovered is that selected PARP inhibitors can ameliorate neural tissue damage and cardiovascular tissue damage, including that following focal ischemia, myocardial infarction, and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

Compounds of the Invention

The PARP inhibitors in the composition of the invention provide impressive protection against vascular damage in stroke. One of the reasons for this superior performance is thought to be that the PARP inhibitors of the invention interfere with more than the NMDA-neurotoxicity and NO-mediated biological pathways.

The PARP inhibitor of the invention can be any PARP inhibitor that has formula I:

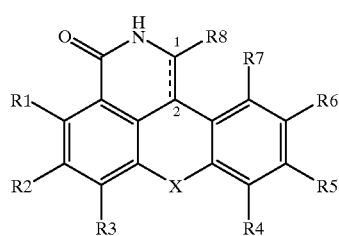

I wherein $R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is N, O, S, or $CR_1R_2$;

with the proviso that X is not O when $R_8$ is Me or H and there is a double bond between $C_1$ and $C_2$; or a pharmaceutically acceptable salt, hydrate, or a mixture thereof.

Particularly preferred embodiments of the invention are:

when $R_1$, $R_2$, $R_3$, $R_4$, $R_5$, $R_6$, $R_7$, or $R_8$ is a substituted or unsubstituted aliphatic or carbocyclic group;

when $R_1$, $R_2$, $R_3$, $R_4$, $R_5$, $R_6$, $R_7$, or $R_8$ is a heterocyclic group;

when $R_1$, $R_2$, $R_3$, $R_4$, $R_5$, $R_6$, $R_7$, and $R_8$ are halo, hydroxyl, nitro or trifluoromethyl;

when one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, and benzyloxy;

when one of $R_1$, $R_2$, or $R_3$ is $C_1-C_9$ straight or branched chain alkyl, $C_2-C_9$ straight or branched chain alkenyl group, $C_3-C_8$ cycloalkyl, $C_5-C_7$ cycloalkenyl, or $Ar_1$;

when one of $R_1$, $R_2$, or $R_3$ is halo, hydroxyl, nitro, or trifluoromethyl;

when one of $R_1$, $R_2$, or $R_3$ is nitro or trifluoromethyl;

when one of $R_4$, $R_5$, $R_6$, or $R_7$ is $C_1-C_9$ straight or branched chain alkyl, $C_2-C_9$ straight or branched chain alkenyl group, $C_3-C_8$ cycloalkyl, $C_5-C_7$ cycloalkenyl, or $Ar_1$;

when one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, and benzyloxy;

when one of $R_4$, $R_5$, $R_6$, or $R_7$ is halo, hydroxyl, nitro, or trifluoromethyl;

when $R_8$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, and benzyloxy;

when $R_8$ is $C_1-C_9$ straight or branched chain alkyl, $C_2-C_9$ straight or branched chain alkenyl group, $C_3-C_8$ cycloalkyl, $C_5-C_7$ cycloalkenyl, or $Ar_1$; and when $R_8$ is halo, hydroxyl, nitro, or trifluoromethyl.

An especially preferred embodiment of the invention is a pharmaceutical composition which comprises:

(i) a therapeutically effective amount of the above-identified compounds; and (ii) a pharmaceutically acceptable carrier.

Another preferred embodiment of the invention is a compound of formula I:

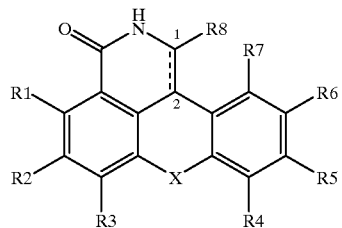

wherein $R_1$, $R_2$, $R_3$, $R_4$, $R_5$, $R_6$, $R_7$, or $R_8$ is hydrogen, $C_1-C_9$ straight or branched chain alkyl, $C_2-C_9$ straight or branched chain alkenyl group, $C_3-C_8$ cycloalkyl, $C_5-C_7$ cycloalkenyl, or $Ar_1$, wherein said alkyl, alkenyl, cycloalkyl, cycloalkenyl or aryl groups may be optionally substituted with $C_3-C_8$ cycloalkyl, $C_3$ or $C_5$ cycloalkyl, $C_5-C_7$ cycloalkenyl, $C_1-C_4$ alkyl, $C_1-C_4$ alkenyl, halo, hydroxyl, nitro, trifluoromethyl, $C_1-C_6$ straight or branched chain alkyl or alkenyl, $C_1-C_4$ alkoxy, $C_1-C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, and benzyloxy;

X is N;

or a pharmaceutically acceptable salt, hydrate, or a mixture thereof.

Particularly preferred embodiments of the invention are:

when $R_1$, $R_2$, $R_3$, $R_4$, $R_5$, $R_6$, $R_7$, or $R_8$ is a substituted or unsubstituted aliphatic or carbocyclic group;

when $R_1$, $R_2$, $R_3$, $R_4$, $R_5$, $R_6$, $R_7$, or $R_8$ is a heterocyclic group;

when $R_1$, $R_2$, $R_3$, $R_4$, $R_5$, $R_6$, $R_7$, and $R_8$ are hydrogen;

when $R_1$, $R_2$, $R_3$, $R_4$, $R_5$, $R_6$, $R_7$, and $R_8$ are halo, hydroxyl, nitro or trifluoromethyl;

when one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, and benzyloxy;

when one of $R_1$, $R_2$, or $R_3$ is $C_1-C_9$ straight or branched chain alkyl, $C_2-C_9$ straight or branched chain alkenyl group, $C_3-C_8$ cycloalkyl, $C_1-C_7$ cycloalkenyl, or $Ar_1$;

when one of $R_1$, $R_2$, or $R_3$ is halo, hydroxyl, nitro, or trifluoromethyl;

when one of $R_1$, $R_2$, or $R_3$ is nitro or trifluoromethyl;

when one of $R_4$, $R_5$, $R_6$, or $R_7$ is $C_1-C_9$ straight or branched chain alkyl, $C_2-C_9$ straight or branched chain alkenyl group, $C_3-C_8$ cycloalkyl, $C_5-C_7$ cycloalkenyl, or $Ar_1$;

when one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_4$, $R_5$, $R_6$, or $R_7$ is halo, hydroxyl, nitro, or trifluoromethyl;

when $R_8$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when $R_8$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and when $R_8$ is halo, hydroxyl, nitro, or trifluoromethyl.

An especially preferred embodiment of the invention is a pharmaceutical composition which comprises:

(i) a therapeutically effective amount of the above-identified compounds; and (ii) a pharmaceutically acceptable carrier.

Yet another preferred embodiment of the invention is a compound of formula I:

I wherein $R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is S;

or a pharmaceutically acceptable salt, hydrate, or a mixture thereof.

Particularly preferred embodiments of the invention are:

when $R_1$, $R_2$, $R_3$, $R_4$, $R_5$, $R_6$, $R_7$, or $R_8$ is a substituted or unsubstituted aliphatic or carbocyclic group;

when $R_1$, $R_2$, $R_3$, $R_4$, $R_5$, $R_6$, $R_7$, or $R_8$ is a heterocyclic group;

when $R_1$, $R_2$, $R_3$, $R_4$, $R_5$, $R_6$, $R_7$, and $R_8$ are hydrogen;

when $R_1$, $R_2$, $R_3$, $R_4$, $R_5$, $R_6$, $R_7$, and $R_8$ are halo, hydroxyl, nitro or trifluoromethyl;

when one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

when one of $R_1$, $R_2$, or $R_3$ is halo, hydroxyl, nitro, or trifluoromethyl;

when one of $R_1$, $R_2$, or $R_3$ is nitro or trifluoromethyl;

when one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

when one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_4$, $R_5$, $R_6$, or $R_7$ is halo, hydroxyl, nitro, or trifluoromethyl;

when $R_8$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when $R_8$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and when $R_8$ is halo, hydroxyl, nitro, or trifluoromethyl.

An especially preferred embodiment of the invention is a pharmaceutical composition which comprises:

(i) a therapeutically effective amount of the above-identified compounds; and (ii) a pharmaceutically acceptable carrier.

Still another preferred embodiment of the invention is a compound of formula I:

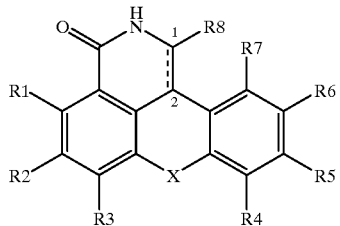

wherein $R_1$, $R_2$, $R_3$, $R_4$, $R_5$, $R_6$, $R_7$, or $R_8$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is $CR_1R_2$;

or a pharmaceutically acceptable salt, hydrate, or a mixture thereof.

Particularly preferred embodiments of the invention are:

when $R_1$, $R_2$, $R_3$, $R_4$, $R_5$, $R_6$, $R_7$, or $R_8$ is a substituted or unsubstituted aliphatic or carbocyclic group;

when $R_1$, $R_2$, $R_3$, $R_4$, $R_5$, $R_6$, $R_7$, or $R_8$ is a heterocyclic group;

when $R_1$, $R_2$, $R_3$, $R_4$, $R_5$, $R_6$, $R_7$, and $R_8$ are hydrogen;

when $R_1$, $R_2$, $R_3$, $R_4$, $R_5$, $R_6$, $R_7$, and $R_8$ are halo, hydroxyl, nitro or trifluoromethyl;

when one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_1$, $R_2$, or $R_3$ is $C_3$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

when one of $R_1$, $R_2$, or $R_3$ is halo, hydroxyl, nitro, or trifluoromethyl;

when one of $R_1$, $R_2$, or $R_3$ is nitro or trifluoromethyl;

when one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

when one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_4$, $R_5$, $R_6$, or $R_7$ is halo, hydroxyl, nitro, or trifluoromethyl;

when $R_8$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when $R_8$ is $C_1$–$C_9$ straight or branched chain alkyl, $C_2$–$C_9$ straight or branched chain alkenyl group, $C_3$–$C_9$ cycloalkyl, $C_5$–$C_7$ cycloalkenyl, or $Ar_1$; and when $R_8$ is halo, hydroxyl, nitro, or trifluoromethyl.

An especially preferred embodiment of the invention is a pharmaceutical composition which comprises:

(i) a therapeutically effective amount of a compound of the present invention; and (ii) a pharmaceutically acceptable carrier.

Yet another preferred embodiment of the invention is a compound of formula I:

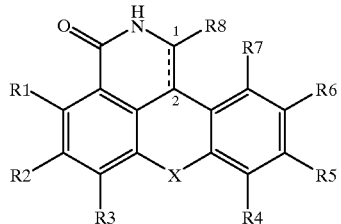

wherein $R_1$, $R_2$, $R_3$, $R_4$, $R_5$, $R_6$, $R_7$, or $R_8$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

X is O;

with the proviso that X is not O when $R_8$ is Me or H and there is a double bond between $C_1$ and $C_2$; or a pharmaceutically acceptable salt, hydrate, or a mixture thereof.

Particularly preferred embodiments of the invention are:

when $R_1$, $R_2$, $R_3$, $R_4$, $R_5$, $R_6$, $R_7$, or $R_8$ is a substituted or unsubstituted aliphatic or carbocyclic group;

when $R_1$, $R_2$, $R_3$, $R_4$, $R_5$, $R_6$, $R_7$, or $R_8$ is a heterocyclic group;

when $R_1$, $R_2$, $R_3$, $R_4$, $R_5$, $R_6$, $R_7$, and $R_8$ are hydrogen;

when $R_1$, $R_2$, $R_3$, $R_4$, $R_5$, $R_6$, $R_7$, and $R_8$ are halo, hydroxyl, nitro or trifluoromethyl;

when one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

when one of $R_1$, $R_2$, or $R_3$ is halo, hydroxyl, nitro, or trifluoromethyl;

when one of $R_1$, $R_2$, or $R_3$ is nitro or trifluorormethyl;

when one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cyaloalkenyl, or $Ar_1$;

when one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when one of $R_4$, $R_5$, $R_6$, or $R_7$ is halo, hydroxyl, nitro, or trifluoromethyl;

when $R_8$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy;

when $R_8$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and when $R_8$ is halo, hydroxyl, nitro, or trifluoromethyl.

An especially preferred embodiment of the invention is a pharmaceutical composition which comprises:

(i) a therapeutically effective amount of a compound of the present invention; and (ii) a pharmaceutically acceptable carrier.

Appropriate PARP inhibitors may be useful in a free base form, in the form of base salts, or in the form of acid addition salts. These three forms are all within the scope of the invention. In practice, the use of a salt amounts to use of the neutral compound. Pharmaceutically acceptable salts within the scope of the invention include those derived from mineral acids, such as hydrochloric acid and sulfuric acid, and those derived from organic acids, such as ethanesulfonic acid, benzenesulfonic acid, p-toluenesulfonic acid, and the like, giving the corresponding hydrochloride, sulfamate, ethanesulfonate, benzenesulfonate, p-toluenesulfonate, and the like, respectively of those derived from the neutral compound.

Examples of suitable inorganic bases for the formation of salts of compounds of the invention include the hydroxides, carbonates, and bicarbonates of ammonia; sodium; lithium; potassium; calcium; magnesium; aluminum; zinc; and the like. Salts may also be formed with suitable organic bases. Organic bases suitable for the formation of pharmaceutically acceptable base addition salts with compounds of the present invention include those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines, such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, "pharmaceutical Salts," *J. Pharm. Sci.*, 66:1, 1–19 (1977).

The acid addition salts of the basic compounds may be prepared either by dissolving the free base of a PARP inhibitor in an aqueous or an aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

It is understood that tautomeric forms, when possible, are included in the invention. For example, the tautomeric forms of the following compounds are exemplary:

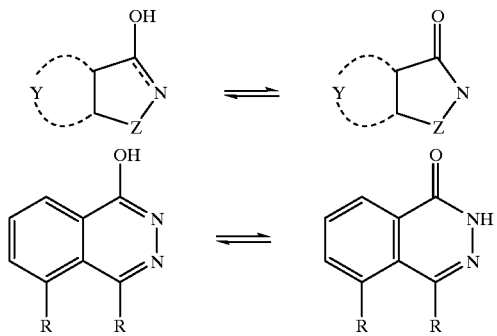

Many of the PARP inhibitors are known and, thus, can be synthesized by known methods from starting materials that are known, may be available commercially, or may be prepared by methods used to prepare corresponding compounds in the literature. See, for example, Suto et al., "Dihydroiso-quinolinones: The Design and Synthesis of a New Series of Potent Inhibitors of Poly(ADP-ribose) Polymerase", *Anticancer Drug Des.*, 6:107–17 (1991), which discloses processes for synthesizing a number of different PARP inhibitors.

Typically, the PARP inhibitors used in the composition of the invention will have an $IC_{50}$ for inhibiting poly(ADP-ribose) synthetase in vitro of 100 $\mu$M to 0.08 $\mu$M, preferably 50 $\mu$M to 0.8 $\mu$M, more preferably 30 $\mu$M to 0.08 $\mu$M, more preferably 10 $\mu$M to 0.8 $\mu$M, more preferably 50 $\mu$M to 10 $\mu$M, more preferably 30 $\mu$M to 10 $\mu$M, more preferably 50 $\mu$M to 10 $\mu$M, more preferably 30 $\mu$M to 5 $\mu$M, and even more preferably 40 nM to 0.8 $\mu$M. The PARP inhibitor 3,4-dihydro-5-[4-(1-piperidinyl)butoxy]1(2H)- isoquinolinone, for example, has been reported to inhibit PARP with an $IC_{50}$ of 40 nM by Suto et al., cited above.

A convenient method to determine $IC_{50}$ of a PARP inhibitor compound is a PARP assay using purified recombinant human PARP from Trevigen (Gaithersburg, Md.), as follows: The PARP enzyme assay is set up on ice in a volume of 100 microliters consisting of 10 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes' incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting.

Methods of Using the Compounds of the Invention

The compounds of the present invention can ameliorate neural tissue damage and cardiovascular tissue damage, including that following focal ischemia, myocardial infarction, and reperfusion injury. Generally, inhibition of PARP activity spares the cells from energy loss, preventing irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of treating a neurological disorder in an animal, comprising administering to an animal a therapeutically effective amount of the above-identified compounds.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke.

Yet another preferred embodiment is when the peripheral neuropathy is caused by Guillain-Barre syndrome.

Still another preferred embodiment is when the demyelinating disease is multiple sclerosis.

Another preferred embodiment is when the neurological disorder relating to neurodegeneration is selected from the group consisting of Alzheimer's Disease, Parkinson's Disease, and amyotrophic lateral sclerosis.

An especially preferred embodiment is a method for preventing a neurological disorder in an animal, comprising administering to a mammal a therapeutically effective amount of the above-identified compounds.

A preferred embodiment is when said neurological disorder is selected from the group consisting of peripheral neuropathy caused by physical injury or disease state, traumatic brain injury, physical damage to the spinal cord, stroke associated with brain damage, focal ischemia, global ischemia, and reperfusion injury.

Another preferred embodiment is when the reperfusion injury is a vascular stroke.

Yet another preferred embodiment is when the peripheral neuropathy is caused by Guillain-Barre syndrome.

Still another preferred embodiment is when the demyelinating disease is multiple sclerosis.

Another preferred embodiment is when the neurological disorder relating to neurodegeneration is selected from the group consisting of Alzheimer's Disease, Parkinson's Disease, and amyotrophic lateral sclerosis.

Yet another preferred embodiment is a method of treating a cardiovascular disease, such as angina pectoris, myocardial infarction, cardiovascular ischemia, and cardiovascular tissue damage related to PARP activation, by administering the compounds of the present invention.

Pharmaceutically Acceptable Carrier

The composition of the invention may be administered via oral, parenteral (intravenous, subcutaneous, intramuscular, intraspinal, intraperitoneal, and the like), rectal, intraventricular, or any other convenient dosage form. When administered parenterally, the composition will normally be in a unit dosage, injectable form (solution, suspension or emulsion) with a pharmaceutically acceptable carrier. Such carriers are preferably non-toxic and non-therapeutic. Examples of such carriers include water; aqueous solutions, such as saline, Ringer's solution, dextrose solution, and Hanks' solution; and nonaqueous carriers, such as fixed oils (e g., corn, cottonseed, peanut, and sesame oil), ethyl oleate, and isopropyl myristate. Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., anti-oxidants, buffers and preservatives.

When administered orally (or rectally), the composition will usually be formulated into a unit dosage form such as a tablet, capsule, suppository or cachet. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like. The composition of the invention is preferably administered as a capsule or tablet containing a single or divided dose of the inhibitor. Preferably, the composition is administered as a sterile solution, suspension, or emulsion, in a single or divided dose.

In another preferred embodiment, the carrier is a solid biodegradable polymer with appropriate time release characteristics. The composition of the invention may then be molded into a solid implant suitable for providing efficacious concentrations of the PARP inhibitors over a prolonged period of time without the need for frequent re-dosing.

The PARP inhibitors are used in the composition in amounts that are therapeutically effective. While the effective amount of the PARP inhibitor will depend on the particular inhibitor being used, amounts of the PARP inhibitor varying from about 1% to about 65% have been easily incorporated into liquid or solid carrier delivery systems.

Doses of the compounds preferably include pharmaceutical dosage units comprising an efficacious quantity of active compound. By an efficacious quantity is meant a quantity sufficient to inhibit PAR and derive the beneficial effects therefrom through administration of one or more of the pharmaceutical dosage units. Preferably, the dose is sufficient to prevent or reduce the effects of vascular stroke or other neurodegenerative diseases. An exemplary daily dosage unit for a vertebrate host comprises an amount of from about 0.001 mg/kg to about 50 mg/kg.

EXAMPLES

Example 1

Approximate IC$_{50}$ Data for Selected PARP Inhibitors

Using the PARP assay described above, the following approximate IC$_{50}$ values are obtained for the following PARP inhibitors:

| PARP Inhibitor | Approximate IC$_{50}$'s |
|---|---|
| 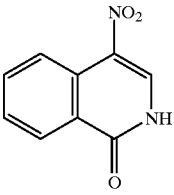 | 5 μM |
| 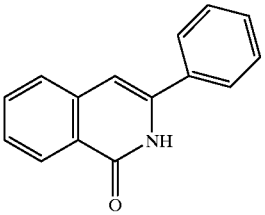 | 30 μm |
| 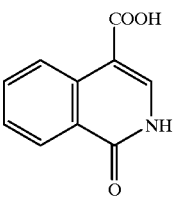 | 10 μM |
| 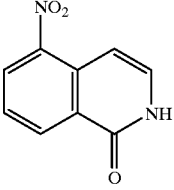 | 10 μM |
| 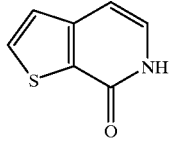 | 50 μM |

-continued

| PARP Inhibitor | Approximate IC$_{50}$'s |
|---|---|
| 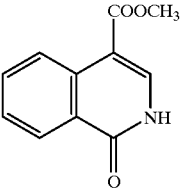 | 0.8 μM |

The invention being thus described, it will be obvious that the same may be varied in many ways. Such variations are not to be regarded as a departure from the spirit and scope of the invention, and all such modifications are intended to be included within the scope of the following claims.

What is claimed is:

1. A compound of formula I:

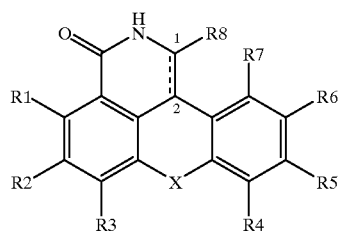

wherein
  $R_1$, $R_2$, $R_3$, $R_4$, $R_5$, $R_6$, $R_7$, or $R_8$ is hydrogen, $C_1$ alkyl, $C_2$–$C_9$ straight or branched chain alkyl, $C_2$–$C_9$ straight or branched chain alkenyl group, $C_3$–$C_8$ cycloalky, $C_5$–$C_7$ cycloalkenyl, or $Ar_1$,
  wherein said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, halo, hydroxyl, nitro, trifluoromethyl, $C_1$ alkyl, $C_2$–$C_6$ straight or branched chain alkyl or alkenyl, $C_1$–$C_4$ alkoxy, $C_2$–$C_4$ alkenyloxy, phenoxy, benzyloxy, or $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$ alkyl, $C_2$–$C_6$ straight or branched alkyl or alkenyl, $C_1$–$C_4$ alkoxy or $C_2$–$C_4$ alkenyloxy, phenoxy, and benzyloxy;
  X is O;
  with the proviso that $R_8$ is not Me or hydrogen when there is a double bond between $C_1$ and $C_2$, and $R_1$–$R_7$ are all hydrogen; or
  a pharmaceutically acceptable salt, hydrate, or a mixture thereof.

2. A pharmaceutical composition which comprises:
  (i) a therapeutically effective amount of the compound of claim 1; and
  (ii) a pharmaceutically acceptable carrier.

3. A method of treating a neurological disorder in an animal, comprising administering to an animal a therapeutically effective amount of the compound of claim 1.

4. The method of claim 3, wherein the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

5. The method of claim 4, wherein the reperfusion injury is a vascular stroke.

6. The method of claim 4, wherein the peripheral neuropathy is caused by Guillain-Barre syndrome.

7. The method of claim 4, wherein the demyelinating disease is multiple sclerosis.

8. The method of claim 4, wherein the neurological disorder relating to neurodegeneration is selected from the group consisting of Alzheimer's Disease, Parkinson's Disease, and amyotrophic lateral sclerosis.

9. A method of treating a cardiovascular disease in an animal, comprising administering an effective amount of the compound of claim 1.

10. The method of claim 9, wherein the cardiovascular disease is selected from the group consisting of angina pectoris, myocardial infarction, and cardiovascular tissue damage related to PARP activation.

11. The pharmaceutical composition of claim 2, wherein the pharmaceutically acceptable carrier is a biodegradable polymer.

12. The compound of claim 1, wherein $R_1$, $R_2$, $R_3$, $R_4$, $R_5$, $R_7$ and $R_8$ are hydrogen.

13. The compound of claim 12, wherein $R_6$ is hydrogen.

14. The pharmaceutical composition of claim 2, wherein $R_1$, $R_2$, $R_3$, $R_4$, $R_5$, $R_7$ and $R_8$ are hydrogen.

15. The pharmaceutical composition of claim 14, wherein $R_6$ is hydrogen.

16. The method of claim 3, wherein $R_1$, $R_2$, $R_3$, $R_4$, $R_5$, $R_7$ and $R_8$ are hydrogen.

17. The method of claim 16, wherein $R_6$ is hydrogen.

18. The method of claim 9, wherein $R_1$, $R_2$, $R_3$, $R_4$, $R_5$, $R_7$ and $R_8$ are hydrogen.

19. The method of claim 18, wherein $R_6$ is hydrogen.

* * * * *